United States Patent [19]

Korpman

[11] Patent Number: 4,886,511
[45] Date of Patent: Dec. 12, 1989

[54] CORRUGATED DISPOSABLE DIAPER

[75] Inventor: Ralf Korpman, Bridgewater, N.J.

[73] Assignee: Personal Products Company, Milltown, N.J.

[21] Appl. No.: 210,610

[22] Filed: Jun. 23, 1988

Related U.S. Application Data

[63] Continuation of Ser. No. 15,245, Feb. 17, 1987, abandoned, which is a continuation of Ser. No. 595,206, Mar. 30, 1984, abandoned.

[51] Int. Cl.$^4$ .............................................. A61F 13/16
[52] U.S. Cl. .................................... 604/365; 604/370; 604/385.2
[58] Field of Search ............... 604/365, 366, 370, 372, 604/373, 385.1, 385.2

[56] References Cited

U.S. PATENT DOCUMENTS

| | | | |
|---|---|---|---|
| 2,062,594 | 12/1936 | McNair | 604/385.2 X |
| 3,779,246 | 12/1976 | Mesek et al. | 604/370 |
| 4,055,180 | 10/1977 | Karami | 604/370 X |
| 4,166,464 | 9/1979 | Korpman | 604/370 |
| 4,323,070 | 4/1982 | Ternstrom et al. | 604/385.2 |
| 4,337,771 | 7/1987 | Pieniak et al. | 604/385.2 X |

Primary Examiner—John D. Yasko
Attorney, Agent, or Firm—Lawrence D. Schuler

[57] ABSTRACT

A corrugated disposable diaper is provided. The diaper has an initially molten liquid-impermeable film as the liquid barrier backing to which is laminated a loosely-compacted cellulosic fibrous batt and a liquid-permeable facing. Multiple strands of elastic are laminated between the initially molten film and a backing fabric in a transverse direction so as to corrugate the fibrous batt and provide a corrugated disposable diaper with longitudinal corrugations.

16 Claims, 3 Drawing Sheets

CORRUGATED DISPOSABLE DIAPER

This is a continuation of application Ser. No. 015,245, filed Feb. 17, 1987, now abandoned, which is a continuation of application Ser. No. 595,206, filed Mar. 30, 1984, now abandoned.

BACKGROUND OF THE INVENTION

The present invention relates to a corrugated disposable diaper. The diaper is formulated with an initially molten film and elastic in such a manner as to firmly stabilize the absorbent batt and subject the batt to corrugation.

Disposable diapers have become commercially important. The structure of these diapers is similar and generally has three basic elements: a liquid-impermeable backing, an absorbent batt, and a liquid-permeable facing. Generally, the backing is of a film such as a polyethylene film. Typical prior art diapers are shown in U.S. Pat. Nos. Re. 26,151 and 3,612,055. Generally, the absorbent batt is smaller in size than the backing or the facing and is sandwiched between the backing and facing, the latter two being laminated one to the other in the marginal portions and substantially coextensive with one another. Frequently, the absorbent batt is a fluff batt of loosely-compacted cellulosic fibers such as wood pulp fibers.

The backing film, typically a polyethylene film, though it is liquid-impermeable, is frequently noisy. Furthermore, the film has a slick feeling to it. Attempts have been made to overcome these drawbacks. For instance, a diaper having a fibrous outer layer is shown in U.S. Pat. No. 3,779,246. While diapers formed in accordance with this patent have improved feel and appearance as compared to diapers having an exposed plastic sheet as the outermost layer, the additional fabric layer coupled with the necessary adhesive introduces additional thickness which in turn can impair flexibility.

Another problem with commercially available disposable diapers is the stability of the fluff batt. Many improvements have been made to stabilize the fluff batt. For instance in U.S. Pat. No. 3,017,304, a paper-like densified skin is provided on the outermost side of the fluff batt, and in U.S. Pat. No. 3,938,522 densified regions, generally in the form of embossed lines, are present to both stabilize the fluff batt and to promote wicking. Whereas these techniques resulted in an improved product, the paper-like densified skin and/or the densified regions tend to stiffen the fluff batt, and it is known that the densified regions are of reduced liquid-holding capacity. All of the known disposable diaper products are laminated products wherein adhesive or glue is required to adhere one layer of the product to another. The adhesive or glue also lends thickness to the product and hence, can make the product less flexible. Furthermore, the adhesive or glue detracts from the absorbent capacity of the product.

An attempt was made to produce a glueless product in U.S. Pat. No. 2,897,108. Tissue sheets were arranged in a stepped fashion, symmetrically one above the other, whereby marginal areas of each successive tissue sheet extended beyond the counterpart edge of the next smaller tissue sheet. A continuous liquid-impermeable plastic film is extrusion coated onto the stacked tissue sheets so as to be coextensive in area with the largest tissue sheet. The film extends across and in contact with the outwardly facing surface of the smallest tissue sheet and the successive marginal areas of the larger tissue sheets and is bonded at least at selected areas to each of the contact tissue sheets. The articles produced by the patent have not met with commercial success for a variety of reasons. First of all, the article is so thin as to be fragile. Secondly, absorbency is entirely inadequate because the tissue sinks into and becomes integral with the film causing substantial loss of potential absorbency. In essence, the product formed by the patent is a sheet of conventional commercially available tissue to which a thin coating of plastic material is applied. The paper-like feel and extremely limited absorptive capacity renders such a product unacceptable as a disposable absorbent product in today's marketplace.

Another problem related to disposable diapers has been the sealing of the diaper about the legs of the wearer, generally, an infant. Elastic has been placed in the leg regions in an attempt to prevent leakage of the diaper. For example, U.S. Pat. Nos. 3,860,003, 4,050,462, and 4,324,245 provide for placement of elastic in the central portion of the diaper in order to assist the diaper in conforming to the leg of the infant. Though a diaper with elastic in the central portion in the margins may improve the fit about the leg, the problem with leakage still exists.

There remains the unsolved need in the marketplace for a disposable diaper product having absorbency characteristics at least equal to those of presently available disposable products, a conformable, comfortable fit, a cloth-like feel, and a product which can be produced by less complex and less expensive processing equipment.

SUMMARY OF THE INVENTION

A corrugated disposable diaper product is provided which has a liquid-permeable facing, a loosely-compacted cellulosic fibrous batt, elastic corrugating means, an initially molten liquid-impermeable film and a fabric backing. The elastic corrugating means is comprised of multiple strands of stretched elastic which are placed transversely to the longitudinal axis of the diaper. These elastic strands are sandwiched between the film and the fabric backing. Preferably, the elastic corrugating means are provided in the central portion of the diaper product so as to gather the product transversely providing longitudinal corrugations in the crotch region. The loosely-compacted cellulosic fibrous batt is smaller in dimension than the backing to provide marginal regions around the batt. The initially molten liquid-impermeable film backing preferably is extruded and the elastic and fibrous batt are placed each on a side of the film almost immediately while the film is still molten and therefore tacky. Next, the liquid-permeable facing is placed over the absorbent batt and the fabric backing is placed on the opposite side of the film and the product is laminated. The facing and the fabric backing are substantially coextensive with the film backing.

This provides a unitary product wherein the fibrous batt is corrugated in such a manner as to provide longitudinal corrugations so that the natural tendency of the diaper product to distribute and wick liquid transversely is instead encouraged to transport and wick the liquid longitudinally, thus using the diaper structure more efficiently.

The corrugated fibrous batt is substantially completely stabilized and will remain corrugated because the strands of stretched elastic are laminated transversely between the initially molten film and backing fabric so firmly that during production, packaging, shipment and subsequent use, the elastic strands do not dislodge. Similarly, the corrugated loosely-compacted cellulosic fibrous batt is stabilized so as not to lump or break up during subsequent shipment and use.

The initially molten liquid-impermeable film backing preferably is extruded generally at a thickness of about 30 mils and may be drawn to a thickness of one mil or more. Suitable films will be described hereinafter.

In addition to having transverse stretched elastic strands placed in the crotch region, these elastic strands may be placed in the waist portion of the diaper product as well.

At the time that the film is extruded, a soft fabric may be placed on the underside of the film and laminated thereto to provide a cloth-like backing.

DETAILED DESCRIPTION OF THE INVENTION

Figure 1:
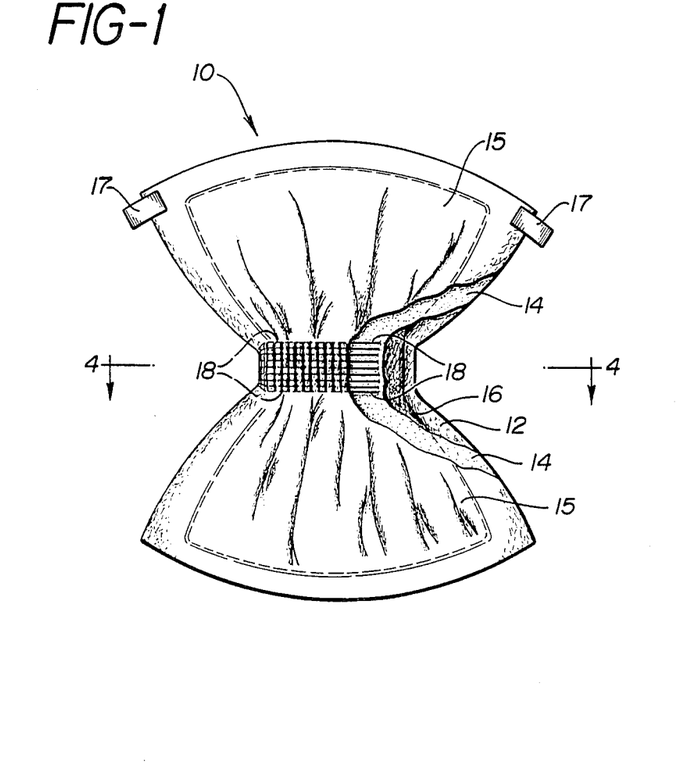
FIG. 1 is a perspective plan view of one embodiment of the present invention with a section broken away for clarity.

Referring now to FIG. 1, a corrugated disposable diaper 10 is illustrated. The view shown in FIG. 1 is from the underside of the diaper. However, a portion is broken away for clarity. A liquid-permeable facing 12 extends the entire length and width of the diaper. An absorbent batt 16 is of smaller dimension than the facing 12 so that there is a margin provided surrounding the absorbent batt. An initially molten film 14 is of the same dimension as the facing 12 so that the facing 12 is adhered to the film 14 in the margins surrounding the batt 16. A multiplicity of elastic strings 18, are placed between the molten film 14 and a fabric backing 15. In the embodiment shown in FIG. 1, the elastic bands are placed only in the central portion so as to gather and corrugate the absorbent batt in the central portion. Tape tabs 17 are affixed to one end to provide a securement means for the diaper product about the waist of the wearer.

Figure 2:
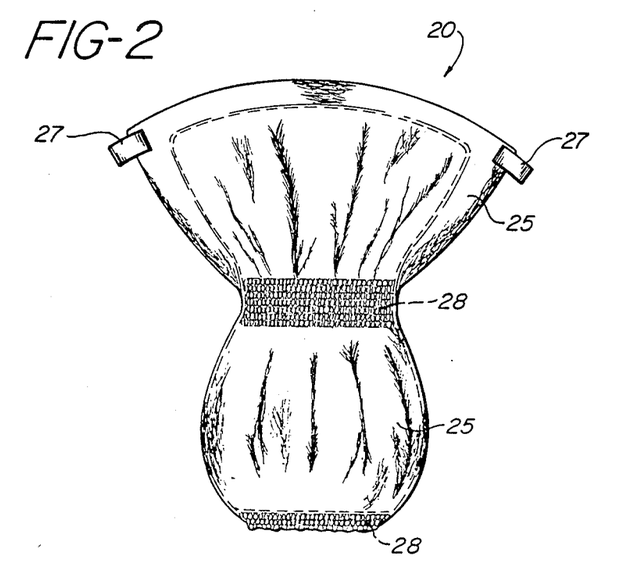
FIG. 2 is a perspective plan view of another embodiment of the present invention.

FIG. 2 illustrates another embodiment of the present invention wherein a diaper 20 is provided. The components are substantially the same as in FIG. 1 except that gathering is provided at regions 28 wherein the diaper is gathered in the central portion and at one end of the waist portion to provide a bell-like configuration. The cloth backing 25 provides a soft external feel for the diaper product. The tape tabs 27 are affixed to one end to secure the diaper about the waist of the wearer.

Figure 3:
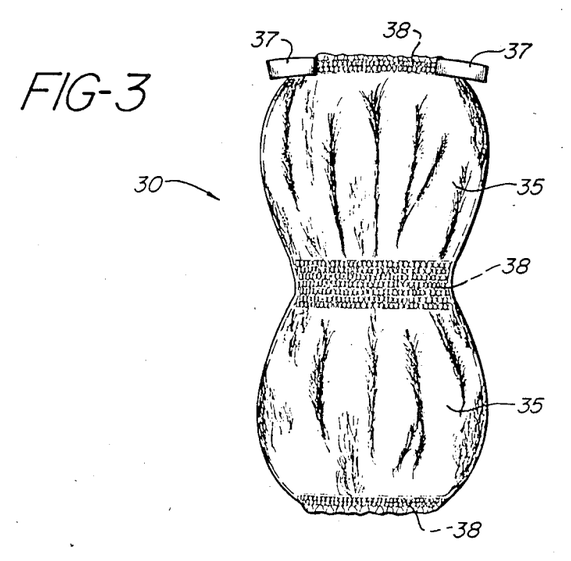
FIG. 3 is a perspective plan view of another embodiment of the present invention.

In FIG. 3, the embodiment differs from FIG. 2 in that elastic is provided at both waist portions as well as in the center at regions 38. A cloth-like backing 35 is provided and tape tabs 37 will secure the diaper about the waist of the wearer.

Figure 4:
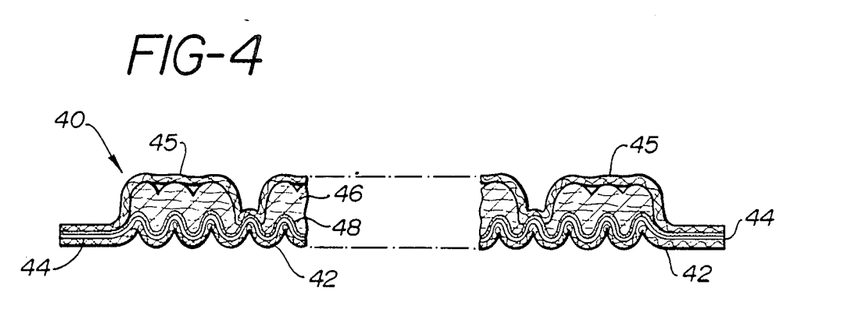
FIG. 4 is an enlarged cross-sectional view taken along line 4—4 of FIG. 1.

FIG. 4 is an enlarged cross-sectional view taken along line 4—4 of FIG. 1. However, in FIG. 4 the under or backside of the diaper is at the bottom of the figure. This portion 40 of the diaper possesses a backing fabric 42. This fabric can be liquid-permeable or impermeable. Elastic bands 44 lie between the backing fabric 42 and the film 48. The corrugated batt 46 is corrugated because it is adhered to the film 48 and the elastic corrugates the film. The surface of the absorbent batt 46 is lightly corrugated and in the present embodiment, holes were placed in the batt before it was put into the product so that the facing 45 could be secured to the film 48, as illustrated at locations 47, so as to secure the facing in the central portion of the diaper where the absorbent batt is corrugated.

Figure 5:
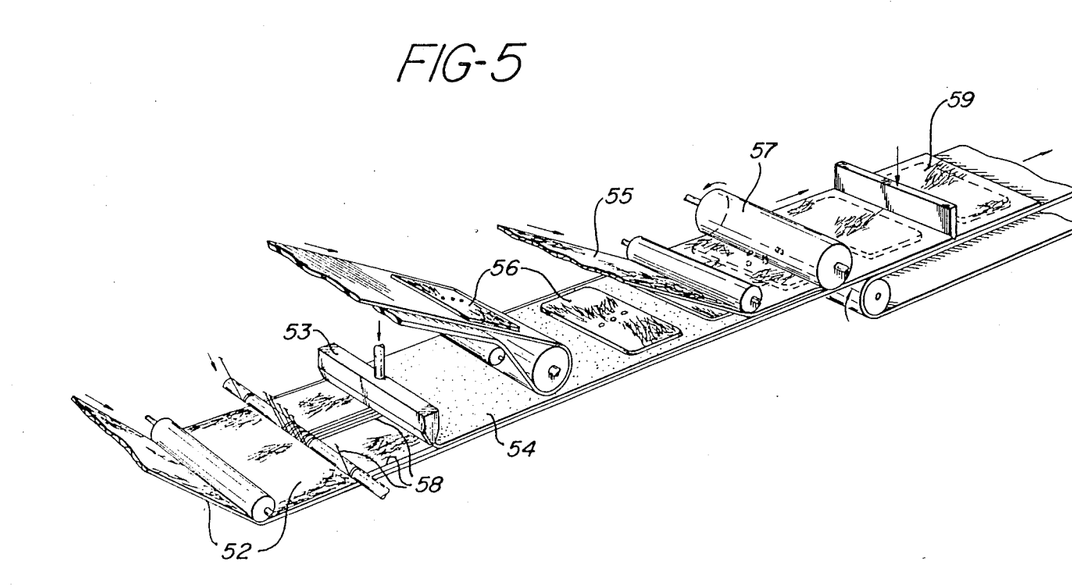
FIG. 5 is a perspective view of a production line for manufacturing an embodiment of the present invention.

FIG. 5 is a perspective view of a production line for producing the embodiment shown in FIG. 3. A fabric 52 is moved along a line and stretched elastic 58 at both sides and in the central portion is placed in contact with the fabric. On top of the fabric and elastic, a molten film 54 is extruded by extruder 53 onto the surface over the entire width of the fabric so as to cover the elastic. Immediately thereafter an absorbent batt 56 is placed on the film intermittently. The absorbent batt has holes in the central portion so that when the facing 55 is placed on top and the entire system is laminated by rolls 57 the facing 55 is secured through the absorbent batt 56 onto the film 54. A cutting knife separates the product into individual disposable diapers 59.

Suitable films for providing the initially molten film generally fall into five groups. The first group contains the plastic films which include polyethylene, ethylenevinyl acetate, polypropylene, polystyrene, polyurethane, polyvinylchloride, polybutylene, copolyesters, vinyls, and acrylics, and other thermoplastic substances or blends thereof. Suitable polyethylenes are the low and medium density polyethylenes. Homopolymers of polyethylene are suitable but many resins are copolymers containing two to 40 percent vinyl acetate. Thus, an ethylene-vinyl acetate copolymer having a high ethylene content is suitable as a plastic for extrusion to provide the initially molten film. Polypropylene is readily processed at extrusion temperatures of about 400°–475° F. Extrusion temperatures for the polystyrene thermoplastics may range from 350°–500° F. Polyurethane is generally extruded as a flexible film or foam. A thin, liquid-impermeable, flexible foam or film of the vinyl copolymers, perhaps the polyvinylchloride, is well known and easy to extrude into the desired, tacky, thin film. Generally, the higher molecular weight resins are used to provide the polyvinylchloride for extrusion.

A suitable copolyester contains at least two identifiable ester units, which may be represented by the formulas:

and wherein x and x' are nuclei of dicarboxylic acids, and y and y' are nuclei of aliphatic diols.

The different ester units may arise from the condensation of two different acids with the same diol, or two different diols with the same acid, or two different acids and two different diols. By "copolyesters" is meant to include random and segmented copolyesters. By "random" is meant that the ester units are not usually in a definite pattern such as in alternating units, or in having a homopolymer of one ester unit joined terminally to a homopolymer of a second ester unit. By "segmented" is meant that there is a polymer block of a given ester unit joined to a polymer block of another ester unit through an ester linkage. Generally, one ester unit of the copolyester is highly crystalline and one substantially less crystalline or even non-crystalline.

Among the aromatic and aliphatic dicarboxylic acids suitable in the copolyester are terephthalic acid, isophthalic acid, oxalic acid, maleic acid, succinic acid, glutaric acid, adipic acid, suberic acid, azelaic acid, sebacic acid, and the like. The aliphatic diols useful in the polyester include ethylene glycol, 1,3-propylene glycol, diethylene glycol, dipropylene glycol, butylene glycol, tetramethylene glycol, trimethylene glycol, and the like. Preferred aliphatic diols are straight chain alkylene diols having from two to four carbon atoms.

Representative copolyesters include poly(ethylene terephthalate-co-ethylene azelate), poly(ethylene terephthalate-co-butylene adipate), poly(ethylene terephthalate-co-1,2-propylene terephthalate), poly(butylene terephthalate-co-butylene isophthalate), poly(ethylene terephthalate-co-ethylene sebacate), poly(ethylene terephthalate-co-tetramethylene terephthalate), poly(ethylene terephthalate-co-ethylene adipate), poly(ethylene terephthalate-co-trimethylene terephthalate), and the like.

When the plastic compositions of this first group are used, it is necessary that the film which is extruded be in its molten state at the time that the absorbent unit and fabric come in contact with the film so that the film is still tacky and lamination can take place.

The second group of suitable materials for films which can be extruded to make the products of the present invention are the thermoplastic elastomeric films. One type which is suitable is an ethylene-vinyl acetate film wherein the vinyl acetate content is high, i.e., from about 40 percent to about 60 percent and the ethylene content is low. Another suitable type is polyurethane. The thermoplastic polyurethane elastomers are prepared from a high molecular weight di-primary diol, a low molecular weight chain extender, and a di-isocyanate. This combination is melt polymerized to form block copolymers with alternating hard and soft segments. The diol is either a polyester or a polyether. Generally, when such a polyurethane is extruded, a single stage extruder is used at temperatures of 320°–430° F.

Polyolefin blends are also suitable to provide a thermoplastic elastomer. These olefinics are blends of a hard component, generally a crystalline polyolefin such as polypropylene or polyethylene, and a soft portion composed of ethylene-propylene rubber. Generally, these olefinic thermoplastic elastomers are extruded at temperatures of 350°–450° F.

Some of the aforementioned copolyesters can be found to be elastomeric. Included in these is poly(ethylene terephthalate-co-ethylene azelate). Elastomeric copolyester products can be formed from non-elastomeric copolyesters. For instance, poly(butylene terephthalate-co-butylene isothalate) copolyester composition can be blended in an amount of about 30 percent by weight with about 70 percent by weight of an elastomer. This alloy is then extruded and can be hot drawn to produce the ester modified elastomeric film.

Particularly suitable thermoplastic elastomers are the thermoplastic elastomeric block copolymers having thermoplastic end blocks and rubbery mid blocks which are designated as A-B-A block copolymers. The expression "A-B-A" block copolymer is intended to embrace all variations of block copolymers with rubbery mid blocks and thermoplastic end blocks. It is also intended to embrace radial block copolymers which may be designated $(A-B)_n X$, wherein X is a poly functional atom or molecule and in which each (A-B) radiates from X in a way that A is an end block. A-B block copolymers sometimes referred to as "simple" block copolymers, in which B forms one end block rather than a mid block, may be included to modify the A-B-A block copolymers and the expression "block copolymer" without qualification is intended to embrace them as well.

The thermoplastic "A" block is generally a polymer of alkenylarenes preferably of styrene or styrene homologues and analogues. The rubbery "B" block is a polymer of a conjugated aliphatic diene of from four to six carbon atoms or a lower alkene of from two to six carbon atoms. Suitable dienes include butadiene, isoprene, and the like. Suitable alkenes include ethylene, butylene, propylene, and the like. In the A-B block copolymers, the B blocks are preferably isoprene. The block copolymers may be linear branched or radial. A branched copolymer is essentially a linear polymer in which branching may occur randomly anywhere in the rubber copolymer chain. A radial block copolymer is characterized and distinguished from the branched linear copolymer in having blocks radiating from a central core.

The individual A block portion has a number average molecular weight of at least 6,000 preferably in the range of from about 8,000 to 30,000, and the B block portion has a number average molecular weight preferably in the range of from about 45,000 to about 180,000. The A block constitute from about five to about 50 percent of the block copolymer. The total block copolymer average molecular weight generally ranges from about 75,000 to about 200,000 for linear copolymers and from about 125,000 to about 400,000 for radial copolymers. In the A-B copolymers, the total molecular weight generally should not exceed about 150,000.

When the "A" block is polystyrene and the "B" block is a polymer of butadiene in an A-B-A type block copolymer, the polymer is frequently referred to as a S-B-S polymer and when the "A" block is a styrene polymer and the "B" block is an isoprene polymer, the polymer is frequently referred to as a S-I-S polymer. Examples of commercially available block copolymers include Solprene 1205 which is a simple S-B (Phillips Petroleum Company) and Shell Chemical Company's Kraton 1102 which is a linear S-B-S and 1107, 1112, and 1117 which are all linear S-I-S.

The elastomeric component of these thermoplastic elastomers may include small amounts of more conventional elastomers but these should not exceed about 25 percent by weight of the elastomeric component. These elastomers may include highly broken down natural rubbers and butadiene-styrene random copolymer rubbers, synthetic polyisoprene, chloroprene rubbers, nitrile rubbers, butyl rubbers, and the like. Potentially elastomeric liquid polymers also may be employed as additives but normally in lower proportions not above about 10 percent by weight of the elastomeric component.

The third group of suitable film forming materials includes alloys which are physical mixtures of structurally different homopolymers or copolymers. Suitable alloys include a mixture of polyethylene and the block copolymers of the thermoplastic elastomer group. Also, polystyrene can be mixed with the block copolymers wherein a high proportion of the block copolymer will be used with a small amount of polystyrene. In addition, copolyesters with elastomers are suitable as taught in U.S. Pat. No. 4,389,444.

The fourth group of suitable film forming materials is a mixture of a thermoplastic elastomer and a low molecular weight (less than 3000) resin modifier. The thermoplastic elastomer is a linear or radial A-B-A block copolymer or mixture of the A-B-A copolymer with one or more simple A-B block copolymers. The A blocks are derived from styrene or styrene homologues and the B blocks are derived from conjugated dienes or lower alkenes. The low molecular weight resins generally are based on polyalphamethylstyrene, polystyrene, polyvinyltoluene and similar aromatic resins. Also included as suitable resins are copolymers thereof, coumarone indene, and related cyclic compounds. The resins are present in an amount of about 10 to about 200 parts for each 100 parts of thermoplastic elastomer. In addition to these resins, small proportions of other resins, i.e., not above about 25% by weight of the elastomeric component, may be added. These resins include hydrocarbon resins, rosin, hydrogenated rosin, rosin esters, polyterpene resins and the like. The resulting films are highly elastic and have a relatively low rubber modulus. The films generally possess high friction properties and are very flexible, extensible, soft and normally exhibit a Gurley stiffness of less than about one at a thickness of one mil.

The last group of suitable films are the pressure-sensitive adhesive films. These films include the hot melt adhesive films. The thermoplastic rubber block copolymers provide suitable formulations for pressure-sensitive adhesive film-formers which can be extruded to produce a highly desirable product. The elastomer will be of a high molecular weight and the resin a low molecular weight. A typical formulation is from 25 to 250 parts by weight of a tackifier resin in proportion to 100 parts by weight of a thermoplastic elastomeric component. Suitable tackifier resins include rosin and rosin derivatives of the abietic acid type or the pimaric acid type. The rosin acids react with alcohols to form esters, e.g., hydrogenated glycerine esters. Hydrocarbon tackier resins are suitable and include low molecular weight polymers containing primarily aromatic, aliphatic or diene monomers. An example of an aliphatic-monomer containing resins is one identified as Wing Tack 95 manufactured and sold by Goodyear Tire and Rubber Company. The terpene resins such as Piccolyte S-100 manufactured and sold by Hercules Chemical Company are also suitable.

Acrylate copolymers are also highly satisfactory. For example, methylmethacrylate-butadiene-styrene provide a suitable film-forming material. Polyacrylates of a proper monomer composition are inherently pressure-sensitive without any compounding. This single component feature has some advantages over the compounded adhesives. Low molecular weight ingredients that can migrate to the surface of an adhesive coating are absent. Adhesive bond is a surface phenomenon, and minimizing the compositional variations is difficult to avoid in multiphase systems, while uniformity is more easily achieved in single component adhesives.

Polyacrylates possess some inherent properties superior to many other polymers used for pressure-sensitive adhesives. The polymer is saturated and resistant to oxidation. It is water white and does not yellow on exposure to sunlight. The resistance to oxidation surpasses that of most polymers used for pressure-sensitive adhesives, except silicones. Monomers with various functional groups can be introduced during polymerization, and an adhesive with various degrees of thermosetting properties can be prepared.

Acrylic adhesives are available as solutions, aqueous emulsion, melts, and 100% reactive solids.

A third type of pressure-sensitive adhesive film involves an ethylene-vinyl acetate based system wherein a tackifying resin is present. Generally the ethylene vinyl acetate copolymer is a random copolymer containing from about 40% to about 60% vinyl acetate by weight. The ethylene vinyl acetate polymer may be used singly or as a mixture with A-B-A or A-B block copolymers. Suitable tackifying resins include rosins and hydrogenated rosins and mixtures thereof.

Suitable film-formers are discussed in the following U.S. Pat. Nos. 3,783,072; 3,932,328; 3,984,509; 4,080,348; 4,178,337; 4,379,806; 4,389,444; and 4,301,255.

The film forming composition of all groups may contain relatively small proportions of various other materials such as antioxidants, heat stabilizers and ultraviolet absorbers, release agents, extenders, plasticizers, pigments, fillers and the like.

The film-formers discussed in Groups II, IV and V can be solvent coated followed by heat lamination or pressure lamination as well as extruded. The film-formers of Group V, which are the adhesive films, can be coated onto the fabric or absorbent unit from water-based systems.

All of the film-formers discussed above can be extruded as a foam as well as a continuous film. Generally a closed cell foam is preferred so that the foam is liquid-impermeable.

Suitable extruding techniques include the single screw extrusion and coextrusion techniques, the primary object being to provide a thin film which at least in its molten form is tacky. Of course, the pressure-sensitive adhesive films are still tacky after formation.

The absorbent unit of the present invention is substantially coextensive with the initially molten film or is smaller in size than the film. The absorbent unit is typically a fluff batt such as that used in conventional disposable diapers. Alternatively, the absorbent unit is a self-contained unit such as a compressed composite unit comprising a resilient fiber fabric, containing superabsorbent and a layer of wood pulp fibers, or the like, which has been compressed to form a highly absorbing unit. Still another form of an absorbent unit is a fabric which contains superabsorbent. All of the absorbent units are capable of absorbing at least about 5 milliliters per gram of the absorbent unit weight.

If the absorbent unit is a fluff batt, generally it is formed of hydrophilic fibers such as rayon fibers, cellulosic fibers, or peat moss, or mixtures thereof, or acrylic fibers, or the like. Cellulosic fibers include wood pulp fibers, cotton linters, and the like. The absorbent unit in the present invention is a fluff batt generally formed of hydrophilic fibers such as rayon fibers, cellulosic fibers or peat moss, or mixtures thereof, or acrylic fibers and the like. Cellulosic fibers include wood pulp fibers, cotton linters, and the like. Other cellulosic fibers that might be used are rayon fibers, flax, hemp, jute, ramie, cotton and the like. Combinations of fibers and particles can be formed in many different ways so long as the absorbent unit will absorb at least about 5 milliliters per gram of weight of the absorbent unit. The absorbent unit preferably is up to about ½ inch in thickness.

A liquid-permeable film or fabric is used as the facing for the diaper product. If the facing is a film, the film is perforated or otherwise treated to permit liquid to permeate the film. Examples of suitable facing materials include polyethylene film which is perforated, polypropylene film, nonwoven polyester fabric, and the like. The film or fabric for the facing is placed in contact with the initially molten film while the film is still tacky so as to permit adhesion of the facing to the initially molten film so as to provide a unitary diaper product.

Likewise, a fabric which need not be liquid-permeable is adhered to the opposite side of the initially molten film. This provides a cloth-like feel backing for the diaper product.

Elastic strands are placed between the fabric backing and the initially molten film at least in the central portion of the diaper product. The strands are placed transverse to the longitudinal axis of the diaper product. The transverse placement of these elastic elements provides a corrugating means for the central portion of the diaper product. Because the absorbent unit is placed in contact with the initially molten film while the film is still tacky, the absorbent unit is also corrugated by the elastic strands. The corrugation of the absorbent unit has many advantages. The gathering of the unit in the central portion of the diaper provides an additional thickness to the diaper product in the region where it is most desired. Furthermore, it provides a shape for the diaper so that the diaper is not as wide in the crotch region and thus, the diaper is conformed more to the body of the infant. Furthermore, the corrugations tend to assist liquid in wicking longitudinally in the diaper rather than transversely. This is an advantage because the absorbent batt has a greater length than width, and thus there is more absorbent capacity throughout the length of the diaper than the width. By transporting the liquid in a longitudinal direction, leakage at the edges is prevented. The product of the present invention is soft, pliable, thereby flexible, noiseless, and provides a substantially 100 percent stable product.

Transverse strands of elastic may also be placed in the waist portions so as to provide an elastic waistband to assist in securing the diaper about the waist of the infant. Such elastic waistband helps prevent the diaper from bowing-out at the waist or from sagging and sliding downward.

The method for making the disposable diaper of the present invention includes bringing the absorbent batt and the fabric in contact with the initially molten film, while the film is still molten (tacky). In the case of non-pressure-sensitive films, it is necessary that the film still be substantially in a hot state. However, with the use of a pressure-sensitive film, the film may be made first and the fabric and absorbent unit combined with it at a later time. There are basically two extrusion type processes which can be used. The first of these is what might be called a "true" extrusion wherein all of the components to form the film are placed in the extruder where they are melted, mixed, and extruded through a die at pressures, temperatures, and conditions to provide a film of 10,000 cps up to 2,000,000 cps. Another method is used when preparing the hot melt pressure-sensitive adhesive wherein the hot melt mix is prepared first and is then placed through an extruder to form the film, or is coated onto the substrate by use of a positive displacement pump and an extrusion die.

Other advantages afforded by the present invention include multiple article production lines, high speed production, production substantially without waste, and modification of a product in the production line with ease and at minimal cost. For instance, a production line might produce the disposable diaper product of FIG. 1 in one instance and with simple modification produce the diaper product of FIG. 3 in a manner of minutes. The absorbent unit can be prepared off-line and consequently will not impede the speed with which the manufacturing can take place. Other components, likewise, such as tape tabs, which are to be placed with the products can be prepared from other production lines and then readily combined either with the initially molten film, while it is still in its tacky state, or simply added to the product at a final point in the production line.

Examples of methods of preparing the disposable diapers of the present invention are as follows. These examples are not intended to be limiting in any way and extensions and modifications thereof without departure from the spirit and scope of the invention will be apparent from one skilled in the art.

Example I

Chemically treated wood pulp fibers such as Rayfloc J are airlaid on a surface to form a loosely compacted cellulosic fibrous batt of approximately ⅜" in thickness and weighing about 45 grams. Such batts are used in conventional disposable diapers as the absorbent unit. The batts are placed on a conveyor and individually come in contact with a molten film of the following type.

Polyethylene pellets are placed in the feedhopper of a single screw extruder (see U.S. Pat. No. 4,178,237). The polyethylene is identified as NA 212 manufactured and sold by U.S. Industrial Chemical Company, New York, N.Y. The feeder places the polyethylene in direct contact with the extruder hot screw heated to a temperature of about 350°–400° F. The molten polyethylene exiting from the extruder is a continuous sheet of about 30 mils thickness which is drawn to a thickness of about one mil or any other predetermined thickness in order to provide a desired weight per unit area.

While the polyethylene film is in its drawn molten state, the previously prepared absorbent batt which is narrower than the film, is placed in contact with the film and a polyester nonwoven fabric having a weight of about 0.7 oz/sq. yd. is placed over the absorbent unit and is substantially coextensive with the film. Substantially, simultaneously, elastic bands are placed on the opposite side of the film from the absorbent batt in contact with the molten film in the central portion of the width of the film, thus, extending entirely transversely across the product. Another polyester nonwoven fabric is placed on the side opposite the absorbent batt against the molten film over the elastic strands and the entire product is laminated.

Conventional adhesive tape tabs are added at each side edge of the product after the product has been severed and is a single unit.

Example II

Particulate components for an elastomeric extrudable film are placed in a feedhopper of an extruder. These components are 97 parts by weight of a styrene-isoprene-styrene elastomer Kraton 1107, 2 parts butyl zimate and 1 part Santovar. Kraton 1107 copolymer is a thermoplastic elastomeric A-B-A (styrene-isoprene-styrene) block copolymer offered by the Shell Chemical Company, wherein the styrene content (that of the A block) is about 12-15 percent, closer to 15 percent, by weight of the block copolymer and the polymer possesses a solution viscosity of about 2000 cps at 25 percent solids in toluene at room temperature (using a Brookfield Viscometer with a number 4 spindle at 60 rpm) and a number average molecular weight of about 110000-125000. The butyl zimate and Santovar are anti-oxidants.

A thin film about two mils thick is extruded and while the film is in a molten state, the absorbent unit and a spun-bonded polypropylene nonwoven facing fabric is placed over the absorbent unit and as a backing over the elastic members as in Example I and the product is laminated. As before appropriate tape tabs are affixed to the side edges of the product.

Example III

The prepared absorbent batt is combined with a molten film alloy consisting of 42 parts by weight of poly-(ethylene terephthalate co-ethylene azelate) and 58 parts by weight of Kraton 1107 discussed in Example II. All components of the diaper product are combined and laminated as in Example I.

Example IV

The film constituents are 40 parts by weight Kraton 1107 and 60 parts by weight polyalphamethylstyrene (Amoco 18-290) manufactured and sold by Amoco Chemical Company. As the film is extruded, elastic strands and a polyester nonwoven fabric are placed in contact with the film on one side while simultaneously an absorbent batt and another layer of polyester are placed on the opposite side of the film. The polyester covers the absorbent batt on the side of the film where the batt contacts the film and the polyester is in contact with the film around the periphery of the batt so as to seal the absorbent batt between the polyester fabric and the molten film. As discussed heretofore, a suitable closure is added after the product has been severed into its individual units.

The resulting product has a fabric feel on both sides and holds at least 150 milliliters of body exudate. The absorbent unit is substantially, completely stabilized and hence even during use, does not break apart or become lumpy in the crotch. Furthermore, the crotch portion of the product has been narrowed by corrugation provided by the elastic elements. The product wicks liquid well from one portion of the batt to another, thus, the liquid holding capacity is substantially fully utilized in the product.

Example V

In this example, pressure-sensitive adhesive films are extruded or applied by hot melt coating techniques to provide a product to which components can be added after the film is no longer molten. Two suitable formulations for pressure-sensitive films appear below:

TABLE I

| | Kraton 1107 | Wing Tack 95 | Butyl Zimate | Santovar A |
|---|---|---|---|---|
| Sample A | 100 | 80 | 2 | 1 |
| Sample B | 100 | 140 | 2 | 1 |

In Table I above, all parts are given in parts by weight. Sample A is a PSA film which is extruded onto a substrate or onto a conveyor after which other components are added later. Sample B may be applied by extrusion or by hot melt coating techniques.

The foregoing is intended as illustrative of the present invention but is not intended as limiting in any way. Numerous variations and modifications may be made without departing from the true spirit and scope of the invention.

I claim:

1. A corrugated disposable diaper comprising:
   (a) a liquid-permeable facing;
   (b) an absorbent unit;
   (c) an initially molten liquid impermeable film having first and second major surfaces;
   (d) elastic corrugating means comprising multiple strands of stretched elastic placed transverse to the longitudinal axis of said diaper; and
   (e) a backing fabric;
   said absorbent unit being disposed adjacent the first major surface of the liquid-impermeable film and being smaller in
   dimension than the liquid-impermeable film so as to provide marginal regions of said liquid-impermeable film around said absorbent unit;
   said liquid-permeable facing being secured to the first major surface of said liquid-impermeable film in said marginal regions so that the absorbent unit is secured between the liquid-impermeable film and the liquid-permeable facing;
   said backing fabric being secured to the second major surface of said liquid-impermeable film; and
   said elastic corrugating means being secured to the second major surface of said initially molten liquid-impermeable film in the central portion of said diaper.

2. The disposable diaper of claim 1 wherein said initially molten film is a plastic film.

3. The disposable diaper of claim 2 wherein said plastic film is selected from the group consisting of polyethylene, ethylene-vinyl acetate, polypropylene, polystyrene, polyurethane, polyvinylchloride, polybutylene, co-polyesters, vinyls, acrylics and mixtures thereof.

4. The disposable diaper of claim 1 wherein said initially molten film is a thermoplastic elastomeric film.

5. The disposable diaper of claim 4 wherein said thermoplastic elastomeric film is selected from the group consisting of ethylene-vinyl acetate, polyurethane, polyolefin blends, co-polyesters, block copolymers and blends thereof.

6. The disposable diaper of claim 1 wherein said initially molten film is a film alloy of structurally different homopolymers or copolymers.

7. The disposable diaper of claim 1 wherein said initially molten film is a mixture of a thermoplastic elastomer and a low molecular weight resin modifier.

8. The disposable diaper of claim 1 wherein said initially molten film is a foam.

9. The disposable diaper of claim 1 wherein said absorbent unit is a loosely compacted cellulosic fibrous batt.

10. The disposable diaper of claim 9 wherein said loosely compacted cellulosic fibrous batt is a batt of wood pulp fibers.

11. The disposable diaper of claim 1 wherein said absorbent unit contains superabsorbent.

12. The disposable diaper of claim 11 wherein said superabsorbent is placed on said initially molten film between said film and said absorbent unit.

13. The disposable diaper of claim 1 further including elastic corrugating means in at least one waist portion of said diaper.

14. The disposable diaper of claim 1 wherein said absorbent unit comprises holes through which the liquid permeable facing is secured to the first major surface of said liquid-impermeable film.

15. The disposable diaper of claim 14 wherein the holes in said absorbent unit are located in the central portion of said diaper.

16. The disposable diaper of claim 1 wherein said initially molten film is a pressure-sensitive adhesive film.

* * * * *